(12) United States Patent
Rathore

(10) Patent No.: US 7,173,073 B2
(45) Date of Patent: Feb. 6, 2007

(54) OPHTHALMIC DEVICES CONTAINING HETEROCYCLIC COMPOUNDS AND METHODS FOR THEIR PRODUCTION

(75) Inventor: Osman Rathore, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 426 days.

(21) Appl. No.: 10/320,572

(22) Filed: Dec. 16, 2002

(65) Prior Publication Data

US 2003/0139490 A1 Jul. 24, 2003

Related U.S. Application Data

(60) Provisional application No. 60/348,585, filed on Jan. 14, 2002.

(51) Int. Cl.
*G02C 7/04* (2006.01)
*G02C 7/02* (2006.01)
*B29D 11/02* (2006.01)

(52) U.S. Cl. ............... 523/106; 523/108; 359/642

(58) Field of Classification Search ............ 523/106, 523/108; 359/900, 642
See application file for complete search history.

(56) References Cited

U.S. PATENT DOCUMENTS

| | | | |
|---|---|---|---|
| 3,854,982 A | 12/1974 | Aelion et al. | |
| 3,916,033 A | 10/1975 | Merrill | |
| 4,330,383 A | 5/1982 | Ellis et al. | |
| 4,920,184 A | 4/1990 | Schafer et al. | |
| 4,973,493 A | 11/1990 | Guire | |
| 5,002,794 A | 3/1991 | Ratner et al. | |
| 5,213,801 A | 5/1993 | Sakuma et al. | |
| 5,256,420 A * | 10/1993 | Tsao et al. ............ | 424/427 |
| 5,350,800 A | 9/1994 | Verhoeven et al. | |
| 5,422,402 A | 6/1995 | Bowers et al. | |
| 5,453,467 A | 9/1995 | Bamford et al. | |
| 5,490,983 A | 2/1996 | Worley et al. | |
| 5,710,302 A | 1/1998 | Kunzler et al. | |
| 5,712,327 A | 1/1998 | Chang et al. | |
| 5,760,100 A | 6/1998 | Nicolson et al. | |
| 5,776,999 A | 7/1998 | Nicolson et al. | |
| 5,789,461 A | 8/1998 | Nicolson et al. | |
| 5,802,818 A | 9/1998 | Eknolan et al. | |
| 5,808,089 A | 9/1998 | Worley et al. | |
| 5,808,098 A | 9/1998 | Kashihara et al. | |
| 5,849,811 A | 12/1998 | Nicolson et al. | |
| 5,902,818 A | 5/1999 | Worley et al. | |
| 5,944,853 A | 8/1999 | Molock et al. | |
| 5,998,498 A | 12/1999 | Vanderlaan et al. | |
| 6,020,491 A | 2/2000 | Wonley et al. | |
| 6,029,808 A | 2/2000 | Peck et al. | |
| 6,077,319 A | 6/2000 | Sun et al. | |
| 6,087,415 A | 7/2000 | Vanderlaan et al. | |
| 6,162,452 A | 12/2000 | Worley et al. | |
| 6,264,936 B1 * | 7/2001 | Sawan et al. ............ | 424/78.26 |
| 6,294,185 B1 | 9/2001 | Worley et al. | |
| 6,469,177 B1 | 10/2002 | Worley et al. | |

FOREIGN PATENT DOCUMENTS

| | | |
|---|---|---|
| EP | 0 196 151 A | 10/1988 |
| EP | 0406161 B1 | 1/1991 |
| GB | 1 391 438 A | 4/1975 |
| GB | 2 072 371 A | 9/1981 |
| GB | 2 218 823 A | 11/1989 |
| JP | 6123860 | 5/1994 |
| JP | 200010055 A | 1/2000 |
| JP | 2000016905 A | 1/2000 |
| JP | 2000107277 A | 4/2000 |
| WO | WO 9300391 A1 | 1/1993 |
| WO | WO 9421698 A1 | 9/1994 |
| WO | WO 98 29463 A | 7/1998 |
| WO | WO 9929750 A1 | 6/1999 |
| WO | WO 9927978 A1 | 10/1999 |
| WO | WO 0022459 A1 | 4/2000 |
| WO | WO 0022460 A1 | 4/2000 |
| WO | WO 0026698 A1 | 5/2000 |
| WO | WO 01/27662 A1 | 4/2001 |
| WO | WO 0127174 A1 | 4/2001 |
| WO | WO 0127662 A1 | 4/2001 |

OTHER PUBLICATIONS

European Search Report, dated May 9, 2003, for European Appln. No. EP 03 25 210.
PCT International Search Report, dated Jun. 3, 2003, for PCT Appln. No. PCT/US03/00772.

* cited by examiner

Primary Examiner—Tae H Yoon

(57) ABSTRACT

This invention relates to ophthalmic devices and methods for their production where the ophthalmic device contain a polymer and at least one heterocyclic compound comprising at least one N—Cl and/or N—Br bond.

18 Claims, No Drawings

OPHTHALMIC DEVICES CONTAINING HETEROCYCLIC COMPOUNDS AND METHODS FOR THEIR PRODUCTION

RELATED PATENT APPLICATIONS

This patent application claims priority of a provisional application, U.S. Ser. No. 60/348,585 which was filed on Jan. 14, 2002.

FIELD OF THE INVENTION

This invention relates to opthalmic devices having antimicrobial properties as well as methods of their production, use, and storage.

BACKGROUND OF THE INVENTION

Contact lenses have been used commercially to improve vision since the 1950s. The first contact lenses were made of hard materials. Although these lenses are currently used, they are not suitable for all patients due to their poor initial comfort and their relatively low permeability to oxygen. Later developments in the field gave rise to soft contact lenses, based upon hydrogels, which are extremely popular today. Many users find soft lenses are more comfortable, and increased comfort levels allow soft contact lens users to wear their lenses for far longer hours than users of hard contact lenses.

Despite this advantage, the extended use of the lenses can encourage the buildup of bacteria or other microbes, particularly, *Pseudomonas aeruginosa*, on the surfaces of soft contact lenses. The build-up of bacteria or other microbes is not unique to soft contact lens wearers and may occur during the use of hard contact lenses as well.

Therefore, there is a need to produce contact lenses that inhibit the growth of bacteria or other microbes and/or the adhesion of bacterial or other microbes on the surface of contact lenses. Further there is a need to produce contact lenses which do not promote the adhesion and/or growth of bacteria or other microbes on the surface of the contact lenses. Also there is a need to produce contact lenses that inhibit adverse responses related to the growth of bacteria or other microbes.

Others have recognized the need to produce soft contact lenses that inhibit the growth of bacteria. In U.S. Pat. No. 5,213,801, the production of an antibacterial contact lens is disclosed, where an antibacterial metal ceramic material is incorporated into a contact lens. This procedure contains a number of steps and may not be suitable for producing all types of lenses in a production environment. The steps include making a silver ceramic material that is fine enough to be used in a contact lens and then forming the lens with the powdered ceramic. However, lenses containing these types of materials often lack the clarity required by contact lens users.

U.S. Pat. Nos. 5,808,089; 5,902,818 and 6,020,491 disclose N-halamine type compounds and their use as biocides. Inclusion of these compounds in ophthalmic devices is not suggested. U.S. Pat. No. 6,162,452 discloses cyclic N-halamine biocidal monomers and polymers. Materials suitable for contact lenses are not disclosed.

Although these methods and lenses are known, other contact lenses that inhibit the growth and/or adhesion of bacteria or other microbes and are of sufficient optical clarity, as well as methods of making those lenses are still needed. It is this need, which this invention seeks to meet.

SUMMARY OF THE INVENTION

This invention includes an opthalmic device comprising, consisting essentially of, or consisting of a polymer and at least one heterocyclic compound comprising at least one N—Cl bond and/or N—Br bond. Preferably said heterocyclic compound comprises at least one substituted five or six membered ring comprising at least one N—Cl bond, at least 3 carbon atoms, 1 to 3 heteroatom nitrogens, 0 to 1 heteroatom oxygen, 0 to 1 heteroatom sulfur and 0 to 3 carbonyls. In another embodiment, the heterocyclic compound is a compound of Formula I

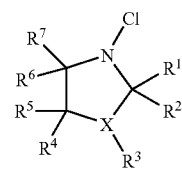

wherein X is independently selected from N, O, C, S;
at least one of $R^1$ and $R^2$, $R^4$ and $R^5$ or $R^6$ and $R^7$ taken together is a carbonyl, $R^3$ is Cl or Br when X is N and the remainder of $R^1$–$R^2$ and $R^4$–$R^7$ are independently selected from hydrogen or substituted or unsubstituted $C_{1-4}$alkyl, Cl, Br, cycloalkyl, substituted or unsubstituted phenyl, substituted or unsubstitute benzyl, ethylenically unsaturated alkyl, acryloxyalkyl, oxygen, nitrogen, sulfur containing groups and the like.

In a preferred embodiment X is N or O, at least one of $R^1$ and $R^2$ or $R^4$ and $R^5$ taken together is a carbonyl, $R^3$ is Cl when X is N and the remainder of $R^1$–$R^7$ are independently selected from the group consisting of H, methyl and carbonyl.

Other suitable heterocyclic compounds include those disclosed in U.S. Pat. No. 6,294,185 and U.S. Pat. No. 6,162,452, the disclosure of which is incorporated herein by reference.

DETAILED DESCRIPTION OF THE INVENTION

Unless specifically defined otherwise, the following terms have the meanings set forth below.

The term heterocyclic compounds include alicyclic ring compounds comprising at least one ring with three to eight carbons and at least one heteroatom per ring.

Cycloalkyl means substituted and unsubstituted alicyclic compounds having three to eight carbon atoms per ring.

Acryloxyalkyl means substituted or unsubstituted acrylates having a $C_{1-3}$ alkyl group adjacent to the oxy group.

Oxygen containing group include any group which comprise oxygen and carbon and/or hydrogen. Suitable oxygen containing groups include hydroxy, oxo, oxa, alkanoyl, haloalkanoyl, carboxy, alkoxycarbonyl groups, acid anhydrides combinations thereof and the like.

Sulfur containing group mean any group which comprise at least one sulfur and hydrogen and may further contain carbon, hydrogen and/or oxygen. Suitable sulfur containing groups include mercapto, alkylthio, sulfate, sulfonic acid groups, combinations thereof and the like. Preferred groups include mercapto and alkylthio.

Nitrogen containing group mean any group which comprises nitrogen and any combination of carbon, hydrogen and/or oxygen. Suitable nitrogen containing groups include amino, cyano, carbomoyl, nitro groups, combinations thereof and the like. Preferred groups are amino and carbamoyl groups.

It should be appreciated that any of the above may be bridging groups through which the heterocyclic compounds are linked to the selected polymer.

In yet another embodiment the heterocyclic compound is selected from 3-chloro-4,4-dimethyl-2-oxazolidinone, 1,3-dichloro-4,4,5,5-tetramethyl-2-imidazolidinone, 1,3-dichloro-5,5-dimethyl-2,4-imidazolidinedione and 1,3-dichloro-2,2,5,5-tetramethyl-4-imidazolidinone and their polymerizable derivatives, 3-chloro-4-(acryloxymethyl)-4-ethyl-2-oxazolidinone and poly(1,3-dichloro-5-methyl-5-(4'-vinylphenyl)hydantoin and combinations thereof.

As used herein, the term "ophthalmic device" includes devices that reside in, on or in front of the eye, such as lenses and related devices such as lens cases. The lenses can provide optical correction or may be cosmetic. The term lens includes, but is not limited to soft contact lenses, hard contact lenses, intraocular lenses, overlay lenses, ocular inserts, optical inserts, spectacle lenses, goggles, surgical glasses and the like. In a preferred embodiment the ophthalmic device is a contact lens and more preferably a soft contact lens. Soft contact lenses are made from hydrogels and silicone elastomers or hydrogels, which include but are not limited to silicone hydrogels and fluorohydrogels. These hydrogels contain hydrophobic and/or hydrophilic monomers that are covalently bound to one another in the cured lens. As used herein the term "lens polymer" means copolymers, homopolymers, or mixtures of said hydrogels and/or silicone elastomers.

As used herein, unless otherwise specified, all weight percents mean weight percent based upon the weight of all components present.

More specifically suitable lens polymers include the soft contact lens formulations described in U.S. Pat. No. 5,710,302, WO 9421698, EP 406161, JP 2000016905, U.S. Pat. No. 5,998,498, U.S. patent application Ser. No. 09/532,943 and U.S. Pat. No. 6,087,415 as well as soft contact lens formulations such as, but are not limited to, etafilcon A, genfilcon A, lenefilcon A, polymacon, aquafilcon A, balafilcon A, and lotrafilcon A. Preferable lens polymers include etafilcon A, balafilcon A, and silicone hydrogels, as prepared in U.S. Pat. No. 5,760,100; U.S. Pat. No. 5,776,999; U.S. Pat. No. 5,849,811; U.S. Pat. No. 5,789,461; WO0127174 A1 and U.S. Pat. No. 6,087,415. These patents are hereby incorporated by reference for the hydrogel compositions contained therein. Lenses prepared from the aforementioned formulations and the heterocyclic compound of the present invention may be coated with a number of agents that are used to coat lenses. For example, the procedures, compositions, and methods of U.S. Pat. Nos. 3,854,982; 3,916,033; 4,920,184; and 5,002,794; 5,712,327; and 6,087,415 as well as WO 0127662, may be used and these patents are hereby incorporated by reference for those procedures, compositions, and methods. In addition to the cited coating patents, there are other methods of treating a lens once it is formed. The lenses of this invention may be treated by these methods, which are illustrated in U.S. Pat. No. 5,453,467; U.S. Pat. No. 5,422,402; WO 9300391; U.S. Pat. No. 4,973,493; and U.S. No. Pat 5,350,800, the disclosure of which are hereby incorporated by reference in their entirety.

Hard contact lenses are made from polymers that include but are not limited to polymers of poly(methyl)methacrylate, silicon acrylates, fluoroacrylates, fluoroethers, polyacetylenes, and polyimides, where the preparation of representative examples may be found in JP 200010055; JP 6123860; and U.S. Pat. No. 4,330,383. Intraocular lenses of the invention can be formed using known materials. For example, the lenses may be made from a rigid material including, without limitation, polymethyl methacrylate, polystyrene, polycarbonate, or the like, and combinations thereof. Additionally, flexible materials may be used including, without limitation, hydrogels, silicone materials, acrylic materials, fluorocarbon materials and the like, or combinations thereof. Typical intraocular lenses are described in WO 0026698; WO 0022460; WO 9929750; WO 9927978; WO 0022459; and JP 2000107277. All of the references mentioned in this application are hereby incorporated by reference in their entirety.

The heterocyclic compounds may be incorporated into the selected polymer by a number of methods. For example, the heterocyclic compound(s) may be dispersed or dissolved into the monomer and/or prepolymer mixtures (reactive mixtures), which are used to form the opthalmic device. The heterocyclic compounds may contain polymerizable groups, which will bond to the selected reactive mixture components during processing or may be devoid of polymerizable groups. Preferred polymerizable heterocyclic compounds have at least one ethylenically unsaturated group that allows covalent incorporation of the compound into the lens matrix or onto the lens surface. Suitable ethylenically unsaturated groups include methacrylates, acrylates, styrenes, mixtures thereof and the like. The ethylenically unsaturated groups may be directly linked to the heterocyclic compounds or may include intervening branched or unbranched alkyl chains, substituted or unsubstituted aryl groups, polyethers, polyamides, polyesters and the like. Heterocyclic compounds which are devoid of polymerizable groups become entangled within the lens material when the monomer is polymerized, forming a semi-interpenetrating network.

Any amount of heterocyclic compound which provides the desired level of inhibition of microbial growth but does not degrade the performance characteristics (such as, but not limited to modulus) of the resulting device may be used. In certain embodiments amounts between about 1 and about 100,000 ppm are desirable, with amounts between about 1 and about 30,000 ppm being preferable and amounts between about 10 and about 25,000 ppm being more preferred. Conventional tools, such as mixing, milling, adjusting the temperature and pressure during mixing, may be used to incorporate the heterocyclic compound into the reactive mixture. Once the heterocyclic compound is incorporated into the reactive mixture, the reactive mixture is used to form the desired device, using known techniques. Thus, where the device is a lens, the reactive mixture may be polymerized and molded or cast into the desired lens shape, molded or cast into a blank and lathed into the desired shape, all using conventional conditions which are well known in the art.

Another method for incorporating the heterocyclic compound into the ophthalmic device is to add a polymerized heterocyclic compound to the reactive mixture and form the mixture into a device as described above. Polymerized heterocyclic compounds that can be incorporated in this manner include as at least one of $R^1$–$R^7$, polymerizable ethylenically unsaturated moiety, preferably methacrylate, acrylate, methacrylamide, styryl, N-vinyl amide, N-vinyl lactams, vinyl carbonates, vinyl carbamates, maleate, or fumarate. The polymer may contain other monomers such as N-vinyl pyrrolidone, HEMA, and the like. In addition, the polymer may contain ethylenically unsaturated moieties such that it can function as a macromer.

Yet another method for incorporating the heterocyclic compound is to deposit the heterocyclic compound on the surface of the opthalmic device. This can be done by numerous ways. For example, a heterocyclic coating composition, including a polymerizable or prepolymerized heterocyclic compound, may be formed and coated onto the opthalmic device and if desired subjected to conditions sufficient to cause polymerization. Suitable heterocyclic coating compositions include, but are not limited to copolymers of HEMA and polymerizable heterocyclic compounds. It should be appreciated that the heterocyclic compound may be included in the lens polymer and coated on the lens.

The coating step may be accomplished by mold transfer, dip coating, spray coating, photo grafting, thermal grafting and the like. Alternatively, the heterocyclic compound may be covalently attached to the ophthalmic device via a wet finishing process, such as is disclosed in U.S. Pat. No. 6,077,319, which is incorporated herein by reference.

Generally a coating effective amount of the coating is used. A coating effective amount of the heterocyclic compound or heterocyclic amine precursor compound is an amount that when contacted with at least one surface of the lens is sufficient to coat that surface so as to impart the desired antimicrobial properties to the surface. The coating may be a homopolymer made from polymerized heterocyclic compound or polymerized heterocyclic amine precursor compound, a copolymer of polymerizable heterocyclic compound or polymerizable heterocyclic amine precursor compound with other polymers, such as but not limited to polyHEMA, polyacrylic acid, PVP, combinations thereof and the like. The desired coating compounds may be dissolved in volatile solvents, which are suitable for coating contact lenses and are known in the art. By antimicrobial properties is meant either or both the ability to significantly reduce, meaning by greater than about 25 percent, either or both the amount of bacteria adhering to the surface and the growth of bacteria adhered to the surface. In the case of contact lenses, generally, the amount contacted with the lens is about 1 μg to about 10 mg, preferably about 10 μg to about 1 mg per lens. The amount of coating resulting per contact lens is about 50 to about 1000 μg. Coatings of the present invention comprise between about 1000 μg heterocyclic compound or heterocyclic amine precursor compound.

It should be appreciated that, for any of the methods of incorporation described above, the heterocyclic compound may be added with the chlorine or bromine atom already attached to the nitrogen or without. If the heterocyclic compound does not contain at least one chlorine when it is incorporated into the device, the device containing the heterocyclic compound will need to be "charged" by contact with a suitable chlorine source. Suitable chlorine source contain anywhere up to about 50,000 ppm sodium or calcium hypochlorite in aqueous solution, from about 10 ppm to 1000 ppm sodium dichloroisocyanurate and/or trichloroisocyanuric acid in aqueous solution and other N-chloramines. The chlorine source also comprises a liquid medium such as, but not limited to, water, deionized water, aqueous buffered solutions, alcohols, polyols, polyethers, glycols and mixtures thereof. Preferred media include deionized water and aqueous buffered solutions. It should be appreciated that as the chlorine concentration increases, the contact time with the solution will decrease. Once the device is charged (or recharged) it is rinsed with an ophthalmically compatible saline solution to remove unbound chlorine and ready the device for use (or reuse). The chlorine charging may take place at any point in the process, but convenient points include during release from the mold, during wet storage, during hydration of a dry stored lens and as a separate step after some period of storage or use. It should be appreciated that a single device, and particularly a single lens could be recharged a multiple of times to extend its antimicrobial effectiveness.

The terms "antimicrobial", "reduction in microbial activity" and "inhibition of microbial activity" refer to a device that exhibit one or more of the following properties—the inhibition of the adhesion of bacteria or other microbes to the ophthalmic device, the inhibition of the growth of bacteria or other microbes on the ophthalmic device, and the killing of bacteria or other microbes on the surface of the ophthalmic device or in a radius extending from the ophthalmic device. The lenses of the invention inhibit the microbial activity by at least 25%. Preferably, the lenses of the invention exhibit at least a 1-log reduction ($\geq$90% inhibition) of viable bacteria or other microbes, more preferably a 2-log reduction ($\geq$99% inhibition) of viable bacteria or other microbes. Such bacteria or other microbes include but are not limited to those organisms found in the eye, particularly *Pseudomonas aeruginosa, Acanthamoeba* species, *Staphyloccus. aureus, E. coli, Staphyloccus epidermidis,* and *Serratia marcesens.* Preferably, said antimicrobial lens is a clear lens, that has clarity comparable to lenses such as those formed from etafilcon A, genfilcon A, lenefilcon A, polymacon, acquafilcon A, balafilcon A, and lotrafilcon A.

The advantages of the antimicrobial lenses of the present invention are many. Without being bound to any particular theory, it is believed that reduction of bacterial activity on the lenses should reduce the occurrence of adverse responses related to bacterial adhesion. It is believed that the heterocyclic compounds of the present invention reduce microbial activity by slow release of small quantities of HOCl, which is an antimicrobial substance produced by the body to kill bacteria. Thus, the lenses of the present invention mimic the eye's chemical response to microbial activity. In addition hypochlorous acid is not known to induce resistance in bacteria. It is further believed that the halamine moiety (N—X, where X is Br or Cl) of the heterocyclic compounds of the present invention interact directly with bacteria to further reduce microbial activity.

The heterocyclic compounds may also be 'recharged' to provide antimicrobial activity throughout the life of the lens. The antimicrobial lenses of the invention. have comparable clarity to lenses such as those formed from etafilcon A, genfilcon A, lenefilcon A, polymacon, acquafilcon A, balafilcon A, and lotrafilcon A.

Further, the invention includes a method of producing an antimicrobial lens comprising a polymer and at least one heterocyclic amine precursor, wherein said hydrogen can be readily replaced with a chlorine or bromine ion, wherein the method comprises, consists essentially of, or consists of the steps of (a) preparing a lens comprising a lens polymer and at least one heterocyclic amine precursor and (b) contacting said lens with a chlorine or bromine source.

The heterocyclic amine precursor has the same structure as the heterocyclic compound defined above, except that the halogen is replaced with a H. Methods for their preparation are known in the art and are generally disclosed in U.S. Pat. No. 6,162,452, which is incorporated herein by reference. The terms lens and chlorine or bromine source, all have the meanings defined above. The heterocyclic amine precursor may be polymerized into the lens polymer, prepolymerized and incorporated into the reaction mixture, which is then polymerized to form an interpenetrating network with the polymer or covalently appended to the lens polymer or coated onto the lens surface either in monomeric or polymeric form or any combination of the above, all as described above.

Typically, the contacting step is conducted for about 120 minutes, though the time may vary from about 1 minute to about 4 hours and at temperatures ranging from about 5° C. to about 130° C. After the contacting step the lenses are washed with several portions of water to obtain a lens that is fully charged with chlorine and substantially free from unbound chlorine.

Still further, the invention includes a lens case comprising, consisting essentially of, a lens case polymer and at least one heterocyclic compound comprising at least one N—Cl or N—Br bond. The term lens case refers to a container that is adapted to define a space in which to hold a lens when that lens is not in use. This term includes packaging for lenses, where packaging includes any unit in which a lens is stored after curing. Examples of this packaging include but are not limited to single use blister packs, multiple use storage cases and the like. Suitable containers may have multiple parts such as the outer container, which holds the lens, a cover and a lens basket, which supports the lens within the chamber inside the container. The heterocyclic compound can be incorporated in any of these parts, but is preferably incorporated into the lens container or the lens basket.

Suitable lens case polymers include, but are not limited to thermoplastic polymeric material, such as polymethylmethacrylate, polyolefins, such as polyethylene, polypropylene, their copolymers and the like; polyesters, polyurethanes; acrylic polymers, such as polyacrylates and polymethacrylates; polycarbonates and the like and is made, or any combination thereof, e.g., molded, using conventional techniques as a single unit.

The heterocyclic compound may be incorporated into the lens container in the same manner that it is incorporated into the antimicrobial lenses of the invention. More specifically, the heterocyclic compound is combined (either as a polymerizable or non-polymerizable compound) with the formulation of the other components, molded and cured. Preferably the heterocyclic compound is present in any or all of the lens case components at about 0.01 to about 10.0 weight percent (based on the initial monomer mix), more preferably about 0.01 to about 1.5 percent. Storing lenses in such an environment inhibits the growth of bacteria on said lenses and adverse effects that are caused by the proliferation of bacteria. Another example of such a lens case is the lens case can be found in U.S. Pat. No. 6,029,808 which is hereby incorporated by reference for the blister pack housing for a contact lens disclosed therein.

Yet still further, the invention includes a method of reducing the adverse effects associated with microbial production in the eye of a mammal, comprising, consisting essentially of, or consisting of providing, for use in or on the eye, an antimicrobial lens wherein said lens comprises polymer and at least one heterocyclic compound comprising at least one N—Cl or N—Br bond.

The terms lens, antimicrobial, lens, $R^1$–$R^7$, all have their aforementioned meanings and preferred ranges. The phrase "adverse effects associated with microbial production" includes but is not limited to, ocular inflammation, contact lens related peripheral ulcers, contact lens associated red eye, infiltrative keratitis, and microbial keratitis.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

Abbreviations

The following abbreviations were used in the examples:
Blue HEMA=the reaction product of reactive blue number 4 and HEMA, as described in Example 4 or U.S. Pat. No. 5,944,853
CGI 1850=1:1 (w/w) blend of 1-hydroxycyclohexyl phenyl ketone and bis (2,6-dimethyoxybenzoyl)-2,4-4-trimethyl-pentyl phosphine oxide
Dl water=deionized water
D3O=3,7-dimethyl-3-octanol
DMA=N,N-dimethylacrylamide
HEMA=hydroxyethyl methacrylate
IPA=isopropyl alcohol
mPDMS=mono-methacryloxypropyl terminated polydimethylsiloxane (MW 800–1000)
Norbloc=2-(2'-hydroxy-5-methacrylyloxyethylphenyl)-2H-benzotriazole
ppm=parts per million micrograms of sample per gram of dry lens
PVP=polyvinylpyrrolidinone (K 90)
TBACB=tetrabutyl ammonium-m-chlorobenzoate
TEGDMA=tetraethyleneglycol dimethacrylate
THF=tetrahydrofuran
TRIS=tris(trimethylsiloxy)-3-methacryloxypropylsilane
TMI=dimethyl meta-isopropenyl benzyl isocyanate
w/w=weight/total weight The following compositions were prepared for use:

Packing Solution

Packing solution contains the following ingredients in deionized $H_2O$:
0.18 weight % sodium borate [1330-43-4], Mallinckrodt
0.91 weight % boric acid [10043-35-3], Mallinckrodt
0.83 weight % sodium chloride [7647-14-5], Sigma
0.01 weight % ethylenediaminetetraacetic acid [60-00-04] (EDTA), Aldrich Phosphate Buffered Saline (PBS)

PBS contains the following in deionized $H_2O$:
0.83 weight % sodium chloride [7647-14-5], Sigma
0.05 weight % monobasic sodium phosphate [10049-21-5], Sigma
0.44 weight % dibasic sodium phosphate [7782-85-6], Sigma Special Packing Solution (SPS)

SPS contains the following in deionized $H_2O$:
0.18 weight % sodium borate [1330-43-4], Mallinckrodt
0.91 weight % boric acid [10043-35-3], Mallinckrodt

EXAMPLE 1

Preparation of 4-hydroxymethyl-4-ethyl-2-oxazolidinone

To a 100 mL round bottom flask, equipped with a magnetic stir bar were added 2-amino-2-ethyl-1,3-propanediol (Aldrich lot 10129PN, 80% w/w, 17.12 g, 0.115 moles), sodium methoxide (Aldrich lot 906641, 0.100 g, 0.0019 moles), and diethyl carbonate (Aldrich lot 10113EU, 17.5 mL, 0.144 moles). The flask was fitted with a reflux condenser and a nitrogen inlet, and the contents were refluxed for 48 hours. The reflux condenser was then replaced with a distillation condenser, and the ethanol formed as a byproduct in the reaction was distilled off. The reaction mixture was diluted with 100 mL ethyl acetate, and then poured into 400 mL diethyl ether. Upon vigorous stirring, a precipitate formed, which was filtered out, washed with diethyl ether (2×50 mL), and dried to obtain a white solid (14.4 g, 86.3% yield). Structure (Formula 2) was confirmed via $^1$H NMR and $^{13}$C NMR data.

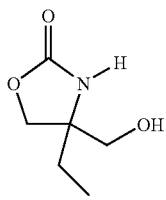

Formula 2. 4-hydroxymethyl-4-ethyl-2-oxazolidinone

EXAMPLE 2

Preparation of 4-acryloxymethyl-4-ethyl-2-oxazolidinone

To a 100 mL round bottom flask equipped with a magnetic stir bar were added 4-hydroxymethyl-4-ethyl-2-oxazolidinone (3.10 g, 21.4 mmol) and 40 mL methylene chloride (Aldrich, A.C.S. reagent grade). Acryloyl chloride (Aldrich lot 14328BO, 1.80 mL, 22.2 mmol) was added via syringe. The reaction flask was fitted with a reflux condenser and a nitrogen inlet, and the contents were refluxed. After 20 hours, a further 0.45 mL of acryloyl chloride was added, and the reaction refluxed for a further 4 hours. Solvents were removed in vacuo using a roto-evaporator to yield a pale yellow oil, which was dissolved in 50 mL methylene chloride and extracted with 0.1 N NaOH (3×50 mL), and saturated sodium chloride solution (1×50 mL). The organic layer was dried over anhydrous sodium sulfate, filtered, and the solvent was removed in vacuo using a roto-evaporator to yield clear, pale yellow oil (2.96 g, 69.5% yield). Structure (Formula 3) was confirmed via $^1$H NMR and $^{13}$C NMR data.

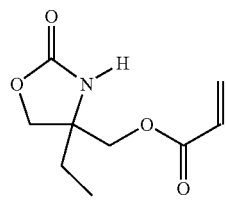

Formula 3. 4-acryloxymethyl-4-ethyl-2-oxazolid inone

EXAMPLE 3

To a dry container housed in a dry box under nitrogen at ambient temperature was added 30.0 g (0.277 mol) of bis(dimethylamino)methylsilane, a solution of 13.75 ml of a 1M solution of TBACB (386.0 g TBACB in 1000 ml dry THF), 61.39 g (0.578 mol) of p-xylene, 154.28 g (1.541 mol) methyl methacrylate (1.4 equivalents relative to initiator), 1892.13 g (9.352 mol) 2-(trimethylsiloxy)ethyl methacrylate (8.5 equivalents relative to initiator) and 4399.78 g (61.01 mol) of THF. To a dry, three-necked, round-bottomed flask equipped with a thermocouple and condenser, all connected to a nitrogen source, was charged the above mixture prepared in the dry box.

The reaction mixture was cooled to 15° C. while stirring and purging with nitrogen. After the solution reaches 15° C., 191.75 g (1.100 mol) of 1-trimethylsiloxy-1-methoxy-2-methylpropene (1 equivalent) was injected into the reaction vessel. The reaction was allowed to exotherm to approximately 62° C. and then 30 ml of a 0.40 M solution of 154.4 g TBACB in 11 ml of dry THF was metered in throughout the remainder of the reaction. After the temperature of reaction reached 30° C. and the metering began, a solution of 467.56 g (2.311 mol) 2-(trimethylsiloxy)ethyl methacrylate (2.1 equivalents relative to the initiator), 3636.6. g (3.463 mol) n-butyl monomethacryloxypropyl-polydimethylsiloxane (3.2 equivalents relative to the initiator), 3673.84 g (8.689 mol) TRIS (7.9 equivalents relative to the initiator) and 20.0 g bis(dimethylamino)methylsilane was added.

The mixture was allowed to exotherm to approximately 38–42° C. and then allowed to cool to 30° C. At that time, a solution of 10.0 g (0.076 mol) bis(dimethylamino)methylsilane, 154.26 g (1.541 mol) methyl methacrylate (1.4 equivalents relative to the initiator) and 1892.13 g (9.352 mol) 2-(trimethylsiloxy)ethyl methacrylate (8.5 equivalents relative to the initiator) was added and the mixture again allowed to exotherm to approximately 40° C. The reaction temperature dropped to approximately 30° C. and 2 gallons of THF were added to decrease the viscosity. A solution of 439.69 g water, 740.6 g methanol and 8.8 g (0.068 mol) dichloroacetic acid was added and the mixture refluxed for 4.5 hours to de-block the protecting groups on the HEMA. Volatiles were then removed and toluene added to aid in removal of the water until a vapor temperature of 110° C. was reached.

The reaction flask was maintained at approximately 110° C. and a solution of 443 g (2.201 mol) TMI and 5.7 g (0.010 mol) dibutyltin dilaurate were added. The mixture was reacted until the isocyanate peak was gone by IR. The toluene was evaporated under reduced pressure to yield an off-white, anhydrous, waxy reactive monomer. The macromer was placed into acetone at a weight basis of approximately 2:1 acetone to macromer. After 24 hrs, water was added to precipitate out the macromer and the macromer was filtered and dried using a vacuum oven between 45 and 60° C. for 20–30 hrs.

EXAMPLE 4

A reaction mixture was formed by adding 80 parts of the components shown in Table 1, in the amounts shown in Table 1 with 20 parts 3,7-dimethyl-3-octanol. Specifically, in the following order macromer, Norbloc 7966, diluent, TEGDMA, HEMA, DMA, TRIS, and mPDMS were added to an amber flask. These components were mixed at 170–300 rpm, at 50–55° C., for 90 to 180 minutes. While maintaining mixing, blue HEMA was added and the components mixed for a further 20 to 75 minutes (at 170–300 rpm, 50–55° C.). Still with mixing, PVP was added and the mixture stirred for another 20 to 140 minutes (at 170–300 rpm, 50–55° C.).

TABLE 1

| Component | Weight Percent |
| --- | --- |
| Macromer (Ex 3) | 17.98 |
| TRIS | 14 |

TABLE 1-continued

| Component | Weight Percent |
|---|---|
| DMA | 26 |
| mPDMS | 28 |
| NORBLOC | 2 |
| TEGDMA | 1 |
| HEMA | 5 |

To 10 g of the monomer mix above, were added 209.7 mg of 4-acryloxymethyl-4-ethyl-2-oxazolidinone (as prepared in Example 2, above), 80 mg of CGI 1850 (Ciba lot# 2W419S), and 100 mg of acetic acid (Fischer Scientific lot #983683). This mixture was mechanically stirred at 50° C. for one hour to homogenize the components. The monomer mix was degassed under vacuum for 30 minutes, and used to make lenses in a nitrogen box at 60–65° C., utilizing Topas alicyclic copolymer (available from Ticona, grade 5013) (front curve, Power –0.50 D) and (back curve) frames under Philips TL03 lamps with 30 minutes of irradiation. The monomer mix and frames were equilibrated in the nitrogen box for 10 minutes prior to assembly. The cured lenses were manually demolded, and immersed in 150 mL of 60:40 mixture of IPA (Mallinckrodt, Ark. (ACS) grade) and deionized (DI) water, respectively. The released lenses were transferred into 100 mL of IPA, and then stepped down into DI water as follows: i) 100 mL of 75:25 (IPA:DI water); ii) 100 mL of 50:50 (IPA:DI water); iii) 100 mL of 25:75 (IPA:DI water); iv) 100 mL of DI water; v) 100 mL of DI water; vi) 100 mL of DI water; vii) 100 mL of DI water; viii) 100 mL of DI water. The lenses were allowed to equilibrate for 20 minutes in between exchanges. Lenses from the last DI water wash were stored in a 100 mL of fresh DI water.

EXAMPLE 5

A hydrogel blend was made from the following monomer mix (all amounts were calculated as weight percent of the total weight of the combination): 17.98% Macromer (Ex 3), 28.0% mPDMS, 14.0% TRIS, 26.0% DMA, 5.0% HEMA, 1.0% TEGDMA, 5.0% PVP, 2.0% Norbloc, 1.25% acetic acid, 1.0% CGI 1850, and 0.02% Blue HEMA; 80 weight percent of the preceding component mixture was further diluted with diluent, 20 weight percent of D3O. The monomer mix was degassed under vacuum at a temperature of 55° C. for at least 30 minutes. The monomer mix was used to prepare lenses using Topas (Ticona, grade 5013) front curves, and polypropylene (Fina, grade EOD 00–11) back curves. The lenses were cured under visible light Philips TL-03 bulbs in a nitrogen atmosphere (<0.5% $O_2$) for 12–15 minutes @ 70±5° C.

The cured lenses were demolded, and then released, leached and hydrated using IPA-deionized water mixtures. The lenses were autoclaved in packing solution for use in microbiological testing.

EXAMPLE 6

Five lenses, prepared as described in Example 4, were treated with 25 mL of dilute sodium hypochlorite solution [1 part Clorox™ bleach (5.25% NaOCl) and 99 parts DI water] by rolling the solution and lenses in a jar on a jar roller for 2 hours. The solution was then decanted, and the lenses were washed with DI water (3×30 mL) by rolling the lenses on a jar roller.

The lenses were autoclaved (30 minutes at 121° C.) in special packing solution.

The autoclaved lenses were analyzed for efficacy against *P. aeruginosa* using the following method. A culture of *Pseudomonas aeruginosa*, ATCC# 15442 (American Type Culture Collection, Rockville, Md.), was grown overnight in a tryptic soy medium. The bacterial inoculum was prepared to result in a final concentration of approximately $1 \times 10^6$ colony forming units/mL (cfu/mL). Three contact lenses were rinsed with phosphate buffered saline (PBS, pH=7.4+/–0.2) to remove residual packing solution. Each rinsed contact lens was placed with 2 mL of the bacterial inoculum into a sterile glass vial, which was then rotated in a shaker-incubator (100 rpm) for two hours at 37+/–2° C. Each lens was removed from the glass vial, rinsed with PBS to remove loosely bound cells, placed into individual wells of a 24-well microtiter plate containing 1 mL PBS, and rotated in a shaker-incubator for an additional 22 hours at 37+/–2° C. Each lens was again rinsed with PBS to remove loosely bound cells, placed into 10 mL of PBS containing 0.05% (w/v) Tween™ 80, and vortexed at 2000 rpm for three minutes, employing centrifugal force to disrupt adhesion of the remaining bacteria to the lens. The resulting supernatant was enumerated for viable bacteria and the results of detectable viable bacteria attached to three lenses were averaged and are reported in Table 2, below. Lenses from Example 4, autoclaved in special packing solution, were used as the controls for microbiological experiments.

TABLE 2

| Ex# | Log CFU[1] | Log reduction |
|---|---|---|
| 4 | 5.84 | Control |
| 6 | 5.07 | 0.77 |

[1]CFU = Colony forming units

Thus, the lenses containing N-halamine showed a 0.77 log reduction in microbial adhesion vs. the lens containing the halamine precursor.

EXAMPLE 7

Six lenses, prepared as described in Example 4, were treated with 100 mL of dilute sodium hypochlorite solution [10 part Clorox™ bleach (5.25% NaOCl) and 90 parts DI water] by rolling the solution and lenses in a jar on a jar roller for 2.5 hours. The solution was then decanted, and the lenses were washed with DI water (3×100 mL) by rolling the lenses on a jar roller, allowing one hour for the first wash and two hours for subsequent washes. The lenses were autoclaved in special packing solution and analyzed for efficacy using the procedures described in Example 6. Lenses made according to Example 5 (containing no precursor) were used as controls. The results are listed in Table 3, below.

TABLE 3

| Ex# | Log CFU | Log reduction |
|---|---|---|
| 5 | 5.96 | Control |
| 7 | 4.41 | 1.55 |

Thus the lenses containing N-halamine showed a 1.55 log reduction vs. the lens containing no halamine.

Since there was no substantial difference noted between the 'log CFU' counts for Example 4 (N-halamine precursor)

and Example 5 (no halamine precursor), the incorporation of N-halamine precursor itself does not confer antimicrobial properties to the lenses.

A comparison of Examples 6 and 7 suggests that increasing the concentration of sodium hypochlorite solution used to treat the lenses may improved efficacy (decrease bacterial adhesion).

What is claimed is:

1. A lens comprising, a polymer and at least one heterocyclic compound comprising at least one N—Cl and/or N—Br bond.

2. The lens of claim 1 wherein said at least one heterocyclic compound comprises at least one five or six membered heterocyclic ring.

3. The lens of claim 1 wherein said heterocyclic compound comprises at least one substituted five or six membered heterocyclic ring comprising within said ring at least one N—Cl bond or N—Br bond, at least 3 carbon atoms, 1 to 3 heteroatom nitrogen containing groups, 0 to 1 heteroatom oxygen, 0 to 1 heteroatom sulfur containing groups and 0 to 3 carbonyls.

4. The lens of claim 1 wherein said at least one heterocyclic compound comprises compound of Formula I,

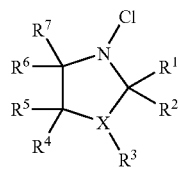

wherein X is independently selected from N, O, C, S;
at least one of $R^1$ and $R^2$, $R^4$ and $R^5$ or $R^6$ and $R^7$ taken together is a carbonyl, R3 is is Cl or Br when X is N and the remainder of $R^1$–$R^7$ are independently selected from the group consisting of hydrogen, substituted or unsubstituted $C_{1-4}$alkyl, Cl, Br, cycloalkyl, substituted or unsubstituted phenyl, substituted or unsubstitute benzyl, ethylenically unsaturated alkyl, acryloxyalkyl, oxygen containing groups, sulfur containing groups and nitrogen containing groups.

5. The lens of claim 2 wherein at least one $R^1$ and $R^2$ or $R^4$ and $R^5$ taken together are O; X is N or O and $R^3$ is Cl when X is N and remaining substituents are independently selected from hydrogen and methyl.

6. The lens of claim 2 wherein said at least one heterocyclic compound is selected from the group consisting of 3-chloro-4,4-dimethyl-2-oxazolidinone, 1,3-dichloro-4,4,5,5-tetramethyl-2-imidazolidinone, 1,3-dichloro-5,5-dimethyl-2,4-imidazolidinedione and 1,3-dichloro-2,2,5,5-tetramethyl-4-imidazolidinone and polymerizable derivatives thereof, 3-chloro-4-(acryloxymethyl)-4-ethyl-2-oxazolidinone and poly(1,3-dichloro-5-methyl-5-(4'-vinylphenyl)hydantoin and mixtures thereof.

7. The lens of claim 2 wherein said lens is a soft contact lens.

8. The lens of claim 2 wherein said at least one heterocyclic compound is present in an amount between about 1 to about 100,000 ppm.

9. The lens of claim 2 wherein said at least one heterocyclic compound is present in an amount between about 1 and about 30,000 ppm.

10. The lens of claim 2 wherein said at least one heterocyclic compound is present in an amount between about 10 and about 25,000 ppm.

11. The lens of claim 7 wherein, the lens is a silicone hydrogel.

12. The lens of claim 7 wherein, the lens is etafilcon A, balafilcon A, acquafilcon A, lenefilcon A, or lotrafilcon A.

13. The antimicrobial lens of claim 7 wherein the lens is etafilcon A.

14. The antimicrobial lens of claim 7 wherein the lens is acquafilcon A.

15. A method of reducing microbial adhesion to a contact lens placed in the eye of a mammal comprising providing an antimicrobial lens comprising, a lens polymer and at least one antimicrobial heterocyclic compound comprising at least one N—Cl and/or N—Br bond.

16. An lens comprising a lens polymer and at least one antimicrobial heterocyclic compound comprising at least one N—Cl and/or N—Br bond, wherein said lens inhibits microbial production by at least 25%.

17. The lens of claim 16 wherein said lens inhibits microbial activity by at least about 50% to at least about 99%.

18. The lens of claim 16 wherein said les inhibits microbial activity by at least about 80% to at least about 99%.

* * * * *